United States Patent [19]

Shiraki et al.

[11] Patent Number: 5,166,420
[45] Date of Patent: Nov. 24, 1992

[54] PROCESS FOR THE PRODUCTION OF HIGH PURITY TEREPHTHALIC ACID

[75] Inventors: Shigemi Shiraki; Kenichi Mizuno, both of Iwakuni, Japan

[73] Assignee: Mitsui Petrochemical Industries, Ltd., Tokyo, Japan

[21] Appl. No.: 784,604

[22] Filed: Oct. 24, 1991

Related U.S. Application Data

[63] Continuation of Ser. No. 107,491, Oct. 8, 1987, abandoned.

[30] Foreign Application Priority Data

Oct. 20, 1986 [JP] Japan ................................ 61-247500

[51] Int. Cl.$^5$ ............................................ C07C 51/487
[52] U.S. Cl. ...................................... 562/487; 562/485; 562/486
[58] Field of Search ......................... 562/485, 486, 487

[56] References Cited

U.S. PATENT DOCUMENTS 3,265,729 8/1966 Olsen et al. ........................... 562/487
4,467,110 8/1984 Puskas et al. ......................... 562/487
4,594,449 6/1986 Takuma et al. ...................... 562/416

FOREIGN PATENT DOCUMENTS 982629 2/1965 United Kingdom ................ 562/486
1261589 1/1972 United Kingdom ................ 562/486

Primary Examiner—Jose G. Dees
Assistant Examiner—Vera C. Clarke
Attorney, Agent, or Firm—Flynn, Thiel, Boutell & Tanis

[57] ABSTRACT

A process for the production of high purity terephthalic acid, by subjecting a crude terephthalic acid product, resulting from the oxidation of a paradialkylbenzene and containing a 4-carboxybenzaldehyde and other impurities at a relatively high level, to an efficient purification with high yield of terephthalic acid. This process comprises subjecting a high temperature aqueous solution of the crude terephthalic acid product to (A) an oxidation treatment with an oxygen-containing gas while feeding oxygen at a feed rate in the range of 0.4–10 moles per mole of the 4-carboxylbenzaldehyde contained in the crude terephthalic acid and then to (B) a treatment with hydrogen.

8 Claims, 1 Drawing Sheet

PROCESS FOR THE PRODUCTION OF HIGH PURITY TEREPHTHALIC ACID

This application is a continuation of U.S. Ser. No. 07/107,491, filed Oct. 8, 1987, now abandoned.

BACKGROUND OF THE INVENTION

1. Field of the Invention

The present invention relates to a process for the production of high purity terephthalic acid and, in particular, to a process in which a crude terephthalic acid containing a relatively large amount of impurities, such as 4-carboxybenzaldehyde (denoted hereinafter as 4-CBA) etc., is treated by a purification step which permits a high yield of terephthalic acid.

2. Description of the Prior Art

Crude terephthalic acid product obtained by liquid phase oxidation of paradialkylbenzene contains in general, relatively large amount of impurities, mostly 4-CBA etc., so that it is not suitable for use in the production of polymer grade polyesters by direct reaction with a glycol due to its untolerable coloration. During the production of crude terephthalic acid, a mild oxidation condition is usually employed in the practice for decreasing the burning loss of a solvent, such as, acetic acid, etc., whereby the amount of impurities is further increased.

There have been proposed techniques for obtaining high purity terephthalic acid by purifying such crude terephthalic acid products containing impurities. Among them, those disclosed in Japanese Patent Publication Nos. 20820/1966, 23447/1968 and 23448/1968 have proposed processes based on the oxidation or hydrogenation treatment of crude terephthalic acid in a suspension in water or in a water/acetic acid solvent. Other proposals based on the treatment by oxidation or reduction of aqueous or water/acetic acid solution of crude terephthalic acid, which brings about higher catalytic efficiency than the above mentioned technique of treating the crude terephthalic acid in a suspension, are found in Japanese Patent Publication Nos. 21819/1967, 16860/1966, 46212/1977, 10051/1978, 32319/1981, 35174/1981, 35653/1981, 51373/1982, 51374/1982 and 51818/1982 as well as in Japanese Patent Application Lay-Open Nos. 1369/1973, 79635/1981 and 103136/1981.

Further proposals found in the prior art include those based on an after-oxidation of the resultant reaction mixture by heating it directly after the reaction, as proposed in Japanese Patent Publication No. 12695/1965; treatment of an aqueous solution of crude terephthalic acid with a catalyst of palladium or zinc, as proposed in Japanese Patent Publication Nos. 29131/1971, 3607/1972, 44213/1972, 13780/1974 and 33189/1974; and treatment of an aqueous alkaline solution of crude terephthalic acid with oxygen, as proposed in Japanese Patent Application Lay-Open No. 113738/1981.

All the techniques for purifying crude terephthalic acid proposed above are effective in some degree when the content of impurities is relatively low, nevertheless they are not always able to stand as satisfactory purification techniques, if the level of impurity content is high. In many cases, the color of crude terephthalic acid will not be improved though the content of 4-CBA, which is the principal impurity, can be reduced. In the prior art processes, the 4-CBA impurity is hardly converted into terephthalic acid and most of it will go to waste, so that no improvement in the yield of terephthalic acid will be expected and the amount of residue resulting from the purification process increases.

For example, according to the technique proposed by Japanese Patent Publication No. 46212/1977, it is described that an original content of 4-CBA of 2,300 ppm can be reduced to 0 ppm by a method in which a high temperature aqueous solution of crude terephthalic acid is treated in the presence of a definite catalyst with a gas mixture containing oxygen and terephthalic acid is then caused to crystallize. By this method, most of the 4-CBA content cannot be recovered by converting it into terephthalic acid and is lost out of the system in a form of benzoic acid due to decarbonylation. Therefore, no increase in the yield of terephthalic acid will be achieved, as the content of 4-CBA increases, though a purification thereof can be attained. Moreover, the color or hue of the so purified terephthalic acid product is not satisfactory. The substance causing deterioration of hue of the product cannot be removed sufficiently by the oxidation treatment and the amount thereof may even be increased on the conditions.

Also, by the purification method based on reduction treatment of aqueous solution of crude terephthalic acid with hydrogen as proposed in the Japanese Patent Publication No. 16860/1966, no increase in the yield of terephthalic acid can be accounted for, since in this case 4-CBA is converted into p-toluic acid.

SUMMARY OF THE INVENTION

An object of the present invention is to provide a process for the production of high purity terephthalic acid, in which the above mentioned problems have been solved.

Another object of the present invention is to provide a process for the production of high purity terephthalic acid, in which the content of impurities can be decreased, even if the crude terephthalic acid contains relatively large amount of impurities, such as 4-CBA, etc., by first preparing an aqueous solution of crude terephthalic acid and subjecting it to an oxidation treatment under a definite condition and treating it subsequently with hydrogen.

A further object of the present invention is to provide a process for the production of high purity terephthalic acid having a superior color in the product.

A still further object of the present invention is to provide a process for the production of high purity terephthalic acid, in which the yield of terephthalic acid can be increased.

Thus, the gist of the present invention consists in a process for the production of high purity terephthalic acid, which is characterized by subjecting a high temperature aqueous solution of crude terephthalic acid produced by oxidation of a paradialkylbenzene to (A) an oxidation treatment under an oxygen-containing gas at a feed rate of oxygen within the range from 0.4 to 10 moles per mole of the 4-carboxybenzaldehyde contained in the crude terephthalic acid and then to (B) a treatment with hydrogen.

BRIEF SUMMARY OF THE DRAWING

The single Drawing appended shows a flow sheet of a typical production apparatus for carrying out the process according to the present invention.

DETAILED DESCRIPTION OF THE INVENTION

Figure 1:
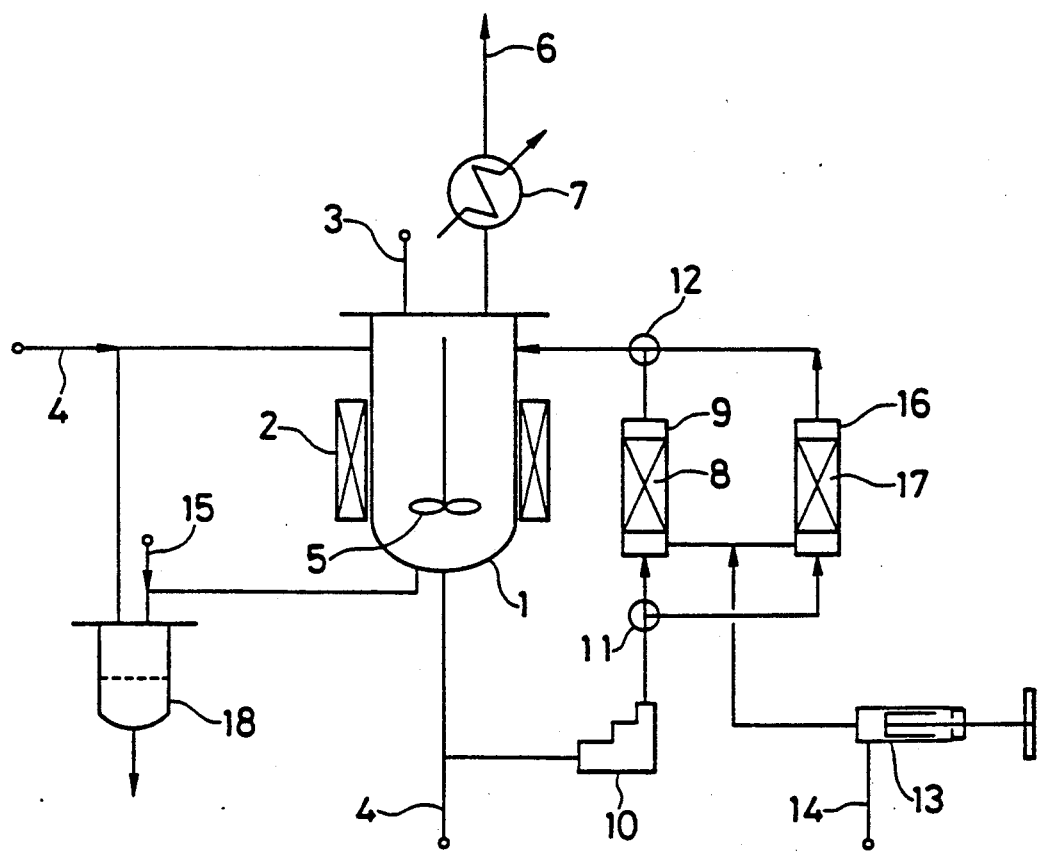

Below, the invention will be described in detail.

Crude Terephthalic Acid

Crude terephthalic acid to be purified in the process according to the present invention is that obtained by oxidizing a paradialkylbenzene, such as p-xylene, in a known method.

The oxidation reaction is performed usually in a solvent, such as acetic acid, propionic acid, butyric acid, isobutyric acid, n-valerianic acid, trimethyl acetic acid, caproic acid and mixtures thereof with water, using an oxygen-containing gas, such as air, in the presence of a catalyst consisting of a heavy metal compound and/or a bromine-containing compound under a high pressure in a liquid phase at a high temperature.

By such an oxidation reaction using, for example, p-xylene as the starting raw material, crude terephthalic acid is formed via p-toluic acid and 4-CBA. In the reaction mixture, formed terephthalic acid will be precipitated as crude terephthalic acid crystals, while incorporating therein impurities, such as the intermediate products of 4-CBA, etc., in a solvent of, for example, acetic acid, etc. Therefore, the crude terephthalic acid product thus obtained includes usually many impurities in addition to 4-CBA.

It is preferable in general that crude terephthalic acid, to be purified in the process according to the present invention, contain at least 1,000 ppm, in particular, more than 2,000 ppm of 4-CBA. This is because the condition of oxidation reaction can be relieved if a crude terephthalic acid product contains a high content of 4-CBA, whereby the burning loss of reaction medium, such as acetic acid, accompanying the oxidation reaction can be suppressed to a minimum. In this respect, it is preferable that the crude terephthalic acid product to be purified according to the present invention should have a high content of 4-CBA, as explained above.

Oxidation Treatment

According to the process of the present invention, an aqueous solution of the crude terephthalic acid product is subjected at high temperature to an oxidation treatment under a definite condition, whereby 4-CBA contained therein as on impurity is oxidized into terephthalic acid without being subjected to decarbonylation, thus achieving a high yield of terephthalic acid.

The crude terephthalic acid product is first dissolved in water to prepare a high temperature aqueous solution. Thus, an aqueous solution of oxidation treatment temperature is prepared by mixing the crude terephthalic acid with water, usually under pressure while heating. While it is preferable to employ pure water, it is permissible that a small amount of reaction medium from the production of crude terephthalic acid product, such as acetic acid, is included.

For the oxidation treatment, an oxygen-containing gas, such as air, is used, if necessary, together with an inert gas, such as nitrogen etc. Here, it is necessary that the feed rate of oxygen into the oxidation treatment system is in the range of 0.4–10 moles, preferably 0.5–5 moles of oxygen per mole of 4-CBA contained in the crude terephthalic acid. If the oxidation treatment is carried out at an oxygen feed rate lower than said lower limit of the range, 4-CBA tends to be converted into benzoic acid by decarbonylation and decrease the yield of terephthalic acid. Within the above mentioned range of oxygen feed rate according to the present invention, almost all of the 4-CBA will be oxidized into terephthalic acid. If the oxygen feed rate exceeds the upper limit of the above mentioned range, oxidation of terephthalic acid occurs with the result of a reduction in its yield and by-production of colored impuriries which are not able to be removed, even by subsequent hydrogen treatment.

Consequently, the oxygen feed rate should be chosen at a value sufficient for the oxidation of 4-CBA but as low as possible, in order to conduct the succeeding reduction treatment advantageously.

In the oxidation treatment, though not essential, a catalyst, such as activated carbon, copper-containing, cobalt-containing or molybdenum-containing carrier catalyst, etc., can be employed in order to promote the reaction. For the latter three, there may be exemplified catalysts in which an oxide of copper, cobalt or molybdenum is held on a carrier, such as $Al_2O_3$, etc. It is also possible to use a catalyst of a double oxide of metals, such as, copper/zinc, cobalt/molybdenum, etc. When using a catalyst, a fixed bed reactor may preferably be employed. As to the condition for the oxidation treatment, usually a concentration of the crude terephthalic acid in water in the range from 100 to 700 g/l, a temperature in the range from 230° to 300° C., a pressure in the range from 30 to 100 Kg/cm$^2$ and a residence time in the range from 2 to 50 minutes may preferably be chosen, although they depend on the purity of the crude terephthalic acid product.

By the oxidation treatment conducted under the condition described above, 4-CBA contained in the crude terephthalic acid will be oxidized into terephthalic acid and the yield of terephthalic acid is thereby increased. However, the hue or color of the crude product based on other impurities is not improved by oxidation treatment and may, in some cases, further deteriorate. This product color can be improved according to the present invention by subsequent hydrogen treatment.

Hydrogen Treatment

The high temperature aqueous solution of crude terephthalic acid which has been subjected to the oxidation treatment is then treated with hydrogen, preferably after passing through a dearation vessel or an oxygen absorbing layer to remove oxygen.

For the hydrogen treatment, an ordinary technique employed for the purification of terephthalic acid product may be applied. As to the preferable condition therefor, a temperature in the range of 270°–300° C., a hydrogen partial pressure in the range of 5–15 Kg/cm$^2$ and a treatment time in the range from 2 to 50 minutes may be employed. For the catalyst for this hydrogen treatment, those which are given in the Japanese Patent Publication No. 16860/1966 can be employed, namely, a catalyst of palladium, ruthenium, rhodium, osmium, iridium or platinum, or platinum black, palladium black, iron-cobalt-nickel, etc. supported on an activated carbon carrier.

By incorporating hydrogen treatment under the condition given above, the product hue due to the impuriries contained in the oxidation treatment solution can also be improved. After the hydrogen treatment, a high purity terephthalic acid product exhibiting superior hue can be obtained by letting the aqueous solution, after treatment, to precipitate terephthalic acid, followed by filtration, centrifugation, etc. Here, it is possible to combine arbitrarily upon a treatment by activated carbon, water wash and so on with the procedures mentioned above.

According to the present invention, a high purity terephthalic acid exhibiting a low content of 4-CBA and a superior hue can be obtained, even if a crude terephthalic acid product having high content of 4-CBA is used as the starting raw material, besides having the advantage of increasing the yield of terephthalic acid due to the capability of recovering 4-CBA in the form of terephthalic acid.

PREFERRED EMBODIMENT OF THE INVENTION

In the following, the invention will be explained concretely by way of Examples.

In the Examples, the content of 4-carboxybenzaldehyde (namely, 4-CBA) contained in the crude terephthalic acid was determined by means of polarographic analysis and the light transmittance for each terephthalic acid product is given in $T_{400}$-value (%) which is a percent transmittance for a light of 400 m $\mu$ passed through a layer of a 2N aqueous potassium hydroxide solution containing terephthalic acid in a concentration of 15% by weight (This is also called an alkaline transmittance).

EXAMPLE 1

An apparatus as shown in FIG. 1 was employed, in which the solution temperature was accurately controlled by an electric heater (not shown) in combination with heat insulation, in order to prevent plugging of lines. In the drawing, valves and pressure control valves are not shown.

Before the experiment, the entire internal gas of the system of FIG. 1 was completely replaced by nitrogen gas. Then, 100 g of a crude terephthalic acid having a 4-CBA content of 5,100 ppm and an alkaline transmittance ($T_{400}$) of 52% were charged in a 2 l slurry dissolution vessel 1 equipped with a heater 2 through a raw material supply line 3, whereupon the entire system was pressurized to a pressure of 80 Kg/cm² gauge. Thereafter, 400 ml of hot water were introduced therein via the hot water inlets 4 and the temperature of the mixture was elevated to 285° C. by the heater 2 with agitation and the agitation was continued by agitator 5 for 30 minutes. The internal pressure of the slurry dissolution vessel 1 was controlled so as to maintain a pressure of 80 Kg/cm² gauge constantly by discharging the gas evolved to outside of the reaction system via a vent line 6 after being passed through a cooler 7.

The contents of the slurry dissolution vessel 1 was circulated through an oxidizing vessel 9 having an internal volume of 80 ml and charged with an activated carbon layer 8 via a pump 10 and two-way valves 11 and 12, while continually introducing air from an air/hydrogen inlet 14 by an injection pump 13. The oxidation treatment, by circulation of the solution through the oxidizing vessel 9, was performed at a constant circulation rate of 5 l/hr for 60 minutes, during which the total amount of air fed was 0.29N l.

Thereafter, the air dissolved in the solution was purged by introducing nitrogen gas therein from line 15 for 10 minutes.

Then, the two-way valves 11 and 12 were actuated and the solution was treated with hydrogen by being circulated through a hydrogen treatment vessel 16 at the same temperature. The hydrogen treatment vessel 16 contained a layer 17 of palladium-on-carbon catalyst in an amount of 80 ml and hydrogen gas was fed intermittently thereto in a total amount of about 0.40N l from the air/hydrogen inlet 14 by the injection pump 13. The duration of hydrogen circulation amounted to 30 minutes.

Subsequently, the system was cooled to 130° C. and the internal pressure was released, whereupon its contents was subjected to pressure filtration through a filter 18 and then to washing with hot water.

The properties of the terephthalic acid obtained from the filter 18 were determined with the results of 4-CBA content being 5 ppm and an alkali transmittance $T_{400}$ of 98%. The total amount of 4-CBA and paratoluic acid in the filtrate was observed to be 0.02 g.

EXAMPLE 2

The procedures of Example 1 were repeated seven times without replacing the catalysts in the hydrogen treatment vessel 16 as well as in the oxidation vessel 9, with the result of almost no change in the material properties of the product obtained.

COMPARATIVE EXAMPLE 1

The same procedures as in Example 1 were repeated with the only exception being that the reaction mixture was cooled to 130° C. directly after the oxidation treatment and subjected to a pressure filtration with the omission of the hydrogen treatment. Here, the catalysts in the oxidation vessel 9 and in the hydrogen treatment vessel 16 were replaced respectively by new ones.

The 4-CBA content of the terephthalic acid product obtained was found to be 100 ppm, but the $T_{400}$-value was decreased to 30%.

COMPARATIVE EXAMPLE 2

The procedures of hydrogen treatment as in Example 1 were repeated without oxidation treatment. The 4-CBA content of the terephthalic acid product obtained was found to be 15 ppm and the $T_{400}$-value amounted to 98%. The total amount of 4-CBA and paratoluic acid was found to be 0.47 g.

COMPARATIVE EXAMPLE 3

The procedures of Comparative Example 2 were repeated five times. In the 5th repetition, the $T_{400}$-value decreased steeply to 81%.

What is claimed is:

1. A process for the production of high purity terephthalic acid comprising the steps of dissolving a crude terephthalic acid in a solvent consisting essentially of water to form an aqueous solution of crude terephthalic acid having a content of 4-carboxybenzaldehyde of at least 1,000 ppm, said crude terephthalic acid being obtained by the oxidation of a paradialkylbenzene, subjecting said aqueous solution of crude terephthalic acid having a content of 4-carboxybenzaldehyde of at least 1,000 ppm to oxidation at a temperature of from 230° to 300° C. and a pressure of 30–100 Kg/cm² by an oxygen-containing gas at a feed rate of 0.4–10 moles of oxygen per mole of 4-carboxybenzaldehyde contained in the crude terephthalic acid, said oxidation being conducted in the presence of a fixed bed catalyst, to obtain a resultant solution, said aqueous solution of crude terephthalic acid having a concentration of 100–700 g of terephthalic acid per liter of aqueous solution, and subjecting the resultant solution to hydrogenation by hydrogen at a temperature in the range of 270°–300° C. and a hydrogen partial pressure of 5–15 Kg/cm$^2$ in the presence of a catalyst to obtain a high purity terephthalic acid.

2. A process according to claim 1, wherein the oxidation is carried out at a residence time of the solution in an oxidation vessel of 2–50 minutes.

3. A process according to claim 1, wherein the hydrogenation is carried out at a treatment duration of 2–50 minutes.

4. A process according to claim 2, wherein the hydrogenation is carried out at a treatment duration of 2–50 minutes.

5. A process according to claim 1, wherein said oxidation is carried out in the presence of a catalyst selected from the group consisting of an activated carbon catalyst, a copper oxide catalyst, a cobalt oxide catalyst, a molybdenum-oxide catalyst, a copper/zinc double oxide catalyst and a cobalt/molybdenum double oxide catalyst.

6. A process according to claim 5, wherein said catalyst is selected from the group consisting of a copper/zinc double oxide catalyst and a cobalt/molybdenum double oxide catalyst.

7. A process according to claim 1, wherein said hydrogenation is carried out in the presence of a catalyst supported on an activated carbon carrier, said catalyst being selected from the group consisting of a palladium catalyst, a ruthenium catalyst, a rhodium catalyst, an osmium catalyst, an iridium catalyst, a platinum catalyst, a platinum black catalyst, a palladium black catalyst and an iron-cobalt-nickel catalyst.

8. A process according to claim 1, wherein said oxygen feed rate is 0.5–5 moles of oxygen per mole of 4-carboxybenzaldehyde.

* * * * *